(12) United States Patent
Law

(10) Patent No.: US 6,759,009 B2
(45) Date of Patent: Jul. 6, 2004

(54) METHOD AND DEVICE FOR CLOTTING TIME ASSAY

(75) Inventor: Wai Tak Law, Moorestown, NJ (US)

(73) Assignee: Portascience Incorporated, Moorestown, NJ (US)

( * ) Notice: Subject to any disclaimer, the term of this patent is extended or adjusted under 35 U.S.C. 154(b) by 10 days.

(21) Appl. No.: 10/138,718

(22) Filed: May 6, 2002

(65) Prior Publication Data

US 2002/0187071 A1 Dec. 12, 2002

Related U.S. Application Data

(60) Provisional application No. 60/288,495, filed on May 4, 2001.

(51) Int. Cl.$^7$ ................................................ G01N 33/86
(52) U.S. Cl. ..................... 422/73; 436/69; 436/164; 436/169; 436/180; 422/56; 422/58; 435/13; 600/369; 73/64.41
(58) Field of Search ................. 436/63, 69, 164, 436/169, 180; 422/56, 58, 73, 100; 435/13; 600/369; 73/64.41

(56) References Cited

U.S. PATENT DOCUMENTS

| | | | |
|---|---|---|---|
| 3,951,606 A | 4/1976 | Moyer et al. | |
| 4,497,774 A | 2/1985 | Scordato | |
| 4,756,884 A | 7/1988 | Hillman et al. | |
| 4,849,340 A | * 7/1989 | Oberhardt ..................... 435/13 |
| 4,948,961 A | 8/1990 | Hillman et al. | |
| 4,952,373 A | 8/1990 | Sugarman et al. | |
| 4,963,498 A | 10/1990 | Hillman et al. | |
| 5,004,923 A | 4/1991 | Hillman et al. | |
| 5,039,617 A | * 8/1991 | McDonald et al. ........... 436/69 |
| 5,087,556 A | 2/1992 | Ertinghausen | |
| 5,110,727 A | 5/1992 | Oberhardt | |
| 5,350,676 A | 9/1994 | Oberhardt et al. | |
| 5,418,141 A | 5/1995 | Zweig et al. | |
| 5,591,403 A | 1/1997 | Gavin et al. | |
| 5,601,995 A | 2/1997 | Exner | |
| 5,628,961 A | 5/1997 | Davis et al. | |
| 5,731,212 A | 3/1998 | Gavin et al. | |
| 5,908,786 A | 6/1999 | Moreno et al. | |
| 6,113,855 A | 9/2000 | Buechler | |
| 6,200,532 B1 | 3/2001 | Wu et al. | |
| 6,451,264 B1 | * 9/2002 | Bhullar et al. ............... 422/100 |

* cited by examiner

Primary Examiner—Maureen M. Wallenhorst
(74) Attorney, Agent, or Firm—Iver P. Cooper; Anne M. Kornbau

(57) ABSTRACT

A self-contained analyzer quantitatively detects a clotting event in a biological fluid. The device includes a base having an open reservoir for receiving the biological fluid. A carrier for a dried activator reagent is located in or adjacent to the open reservoir. The biological fluid reconstitutes the dried reagent and starts the clotting process. During the clotting process the fluid travels through a capillary flow channel lined with a precision woven fabric. When clotting is completed, the woven fabric stops the flow of the fluid. A colored bar formed by the fluid flowing through the capillary channel indicates the length of time required for clotting of the sample.

12 Claims, 1 Drawing Sheet

METHOD AND DEVICE FOR CLOTTING TIME ASSAY

CROSS-REFERENCE TO RELATED APPLICATIONS

The present invention claims priority from provisional application No. 60/288,495, filed May 4, 2001, the entire contents of which are hereby incorporated by reference.

MENTION OF GOVERNMENT SUPPORT

This invention was made with government support under grant #1R43HL67001-01 awarded by the National Institutes of Health. The government has certain rights in this invention.

BACKGROUND OF THE INVENTION

1. Field of the Invention

The present invention relates generally to clotting time testing, such as prothrombin time (PT) testing and, more specifically, to disposable clotting time testing devices and methods for assaying the clotting time of biological fluids without the aid of an instrument.

2. Description of the Background Art

Keeping blood in a fluid state, termed hemostasis, requires a subtle balance of pro- and anti-coagulants. Procoagulants prevent excessive bleeding by blocking blood flow from a damaged vessel, whereas anticoagulants prevent clots from forming in the circulation which could otherwise block blood vessels and lead to myocardial infarction.

The biochemical sequence leading to a blood clot is termed the coagulation cascade. The mechanism is based on catalytic conversion of fibrinogen, a soluble plasma protein, to insoluble fibrin. The enzyme catalyzing this reaction is thrombin, which does not permanently circulate in the blood in an active form, but exists as prothrombin, the inactive precursor of thrombin. Conversion to thrombin occurs in the presence of calcium ions and tissue thromboplastin. This mechanism is known as the extrinsic pathway. A second, more complex, intrinsic pathway is activated by clotting factors associated with platelets.

There are an estimated two million patients with cardiovascular disease in the United States who are currently on anticoagulation therapy. Thirty percent of these patients are "high risk" for subsequent complications. Complications, when they occur, account for 400,000 hospitalizations and 200,000 deaths annually in the United States. Therefore, it is important to monitor these patients frequently to help prevent hemorrhagic and thromboembolic complications. Monitoring is accomplished by measuring the patient's blood clotting time, more specifically, prothrombin time, usually weekly. During initial adjustment of anticoagulation medication, testing may occur more frequently than weekly.

Diagnosis of hemorrhagic conditions such as hemophilia, where one or more of the twelve blood clotting factors may be defective, can be made using a coagulation test. In addition, several tests have been developed to monitor the progress of thrombolytic therapy. Other test have been developed to signal a prethrombolytic or hypercoagulable state, or monitor the effect of administering protamine to patients during cardiopulmonary bypass surgery.

Currently, all prothrombin time testing is conducted on some form of instrumentation. These instruments range from desktop units used in clinical laboratories to small portable units designed to be used for point of care applications. The convenience of self-testing at home is the most effective means for driving patient compliance. Although portable instruments designed for home use are available, the high initial cost, the complexity of quality control, and the inconvenience of refrigerated storage of the reagent has not created a wide acceptance of these instruments by the patients. Thus, there exists a need for a non-instrumented clotting time test device that is simple to use, light in weight, inexpensive, and accurate.

The prothrombin test was first described by A. J. Quick, *Am. J. Med. Sci* 190:501 (1935), and involved mixing tissue thromboplastin with blood, under controlled conditions, to initiate coagulation via the extrinsic pathway. The standard laboratory technique for coagulation testing usually uses a turbidimetric method, such as described in U.S. Pat. No. 4,497,774. In this test, citrated plasma is mixed with tissue thromboplastin at 37° C., and measurement is based upon optical density. An alternative method using calorimetric measurement is also described by Beker et al. in *Hemostatis* 12:73, 1982.

Moyer et al., in U.S. Pat. No. 3,951,606, first disclosed a manually operable disposable device which has a uniform bore reaction tube and limiting orifice for prothrombin time testing. A blood sample is applied to the device and mixed with activator reagent. The gravity-assisted flow travels through the reaction tube and halts when the blood clots. The distance traveled by the sample is proportional to the prothrombin time. Unfortunately, this device is difficult to fabricate and the end point generated is unstable because the flow continues slowly even after clotting has occurred.

U.S. Pat. No. 5,628,961, discloses an apparatus for conducting a variety of assays that are responsive to a change in the viscosity of a fluid sample. A reversible pump is used to move the fluid sample, making this device rather cumbersome.

Point of care whole blood prothrombin time instruments are described in U.S. Pat. Nos. 4,756,884 and 4,963,498. These instruments include cassettes with capillary channels in which the instrument monitors the change of flow of clotting blood. U.S. Pat. No. 5,004,923, describes additional optical and mechanical features of the instrument and cartridge that perform prothrombin time assays.

Other methods for measuring blood clotting include an instrument that measures the change of the field of magnetic particles inside disposable channels (U.S. Pat. No. 5,350,676); an instrument with miniature pumps and disposable cassettes with narrow restriction that plug up upon the clotting of blood (U.S. Pat. Nos. 5,591,403 and 5,731,212); a solid phase membrane with a dry reagent that contains a substrate which produces a detectable signal upon activation by a component of the coagulation pathway (U.S. Pat. No. 5,418,141); an instrument that uses a liquid crystal to measure clotting (U.S. Pat. No. 5,908,786); and piezoelectric means to detect clotting (U.S. Pat. No. 6,200,532).

U.S. Pat. No. 5,087,556, describes a non-instrumented measuring device which uses a flow channel with a detection film inside. This device, however, is not for use in conducting a clotting test. U.S. Pat. No. 4,756,884, teaches the use of a capillary channel containing reagent for estimating the flow change of blood. Although the surface energy inside the capillary channel, was defined, there is no description of how to control the flow stoppage of the blood upon clotting.

U.S. Pat. No. 6,113,855, describes a capillary flow channel including capillary-inducing structures, hexagonal and other geometric shapes, in which one end of the flow channel is deeper than the other end. There is no indication that this device can be used for clotting assays. Exner, in U.S. Pat. No. 5,601,995, discloses a method for estimating coagulation time by measuring the extent and rate of spreading of a blood sample deposited onto a porous sheet. Zweig et al., in U.S. Pat. No. 5,418,141, disclose test articles suitable for prothrombin time testing that comprise a solid phase membrane having dry thromboplastic immobilized thereon or within. A blood sample is applied to the application side, and a fluorescent signal is measured on the other side of the membrane.

Oberhardt et al. disclose another format in Y U.S. Pat. Nos. 5,110,727 and 5,350,676, based upon the use of magnetic particles mixed into a dry reagent contained within a flat capillary chamber. An applied oscillating magnetic field causes the particles to oscillate once the reagent is dissolved in blood. When the blood clots, the motion is diminished and the prothrombin time is estimated. Davis et al., in U.S. Pat. No. 5,628,961, disclose a method and device that respond to changes in the viscosity of a fluid sample using a reciprocating pump.

Thus, there remains a need for an inexpensive, non-instrumented disposable device for quantitative determination of prothrombin time that is both accurate and simple to use.

SUMMARY OF THE INVENTION

It is an object of the present invention to overcome the aforesaid deficiencies in the background art.

It is another object of the present invention to provide a self-contained quantitative analytical device that detects the end point of a clotting and agglutinating process.

It is another object of the present invention to provide a method for quantifying a clotting or agglutinating event.

The present invention relates to an analytical device for detecting a clotting or agglutinating event in a clottable or agglutinatable biological fluid comprising:

a. a capillary flow channel means through which the fluid may flow and in which the clotting or agglutinating event can occur;

b. A reagent to react with the clottable or agglutinatable biological fluid to produce a clot; and c. A control means for controlling the flow rate of the clottable biological fluid and the usual appearance of the clot.

In a preferred embodiment, the device of the present invention contains a sample accepting area, a dried thromboplastic activator which optionally is impregnated on a reagent pad, a capillary channel that has a hydrophilic inner surface for drawing the sample along the channel and a hydrophilic woven fabric surface that controls the flow, provides wicking action, and allows the clotted or agglutinated mixture to anchor onto the fabric surface and stop flow.

The present invention also provides a method for quantifying the time for a clotting or agglutinating event using the device of the present invention. A sample fluid is received in the sample accepting area, and the sample fluid is mixed with reagent. The mixture is drawn through the capillary channel by capillary and/or wicking action. The flow of the sample mixture through the flow channel stops when the clotting or agglutinating event occurs.

For purposes of the present invention, "clotting event" and "agglutinating event" mean the endpoints of clot formation or agglutination, and can be used interchangeably.

BRIEF DESCRIPTION OF THE DRAWINGS

FIG. 2 shows a side view of the device according to the present invention.

FIGURE LEGENDS

| | |
|---|---|
| 100 | clotting measurement device |
| 10 | hydrophilic film bottom |
| 20 | spacers |
| 30 | precision woven fabric |
| 40 | top film |
| 50 | reagent pad |
| 60 | capillary flow channel |
| 70 | open reservoir |

DETAILED DESCRIPTION OF THE PREFERRED EMBODIMENTS OF THE INVENTION

Figure 1:
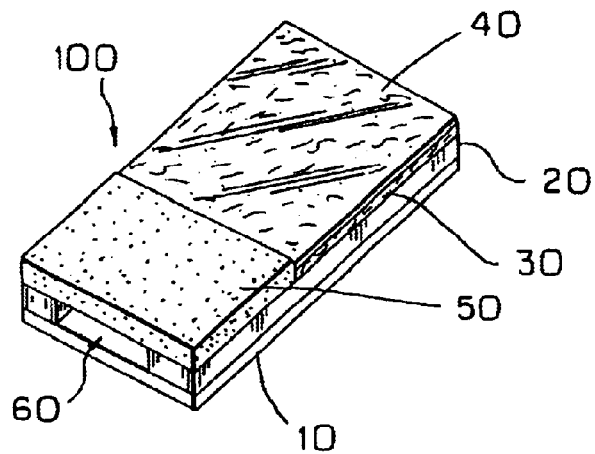
FIG. 1 shows a plan view of the device according to the present invention.

The device of the present invention is a self-contained analyzer that quantitatively detects a clotting event in a clottable biological fluid such as whole blood, or an agglutinating event in a sample, such as agglutination of latex beads. As shown in FIG. 1, the device 100 comprises a bottom 10 made of hydrophilic film, spacers 20, woven fabric 30, and a clear top film 40. An optional reagent pad 50 is located at the front of the capillary flow channel 60.

In a preferred embodiment of the invention the bottom 10 is made of a hydrophilic film. This hydrophilic film is present in order to make it possible for the sample fluid to traverse the device until a clotting event occurs. However, the hydrophilic surface may be any surface which is in contact with the precision woven fabric, or other device which stops the sample fluid flow once a clotting or agglutinating event occurs, which hydrophilic surface serves to help the sample fluid traverse the device. The top film also enhances the capillary flow of the sample through the device.

In another embodiment, the reagent is coated or layered directly onto the bottom of the device in a position in which the sample contacts the reagent immediately on introduction into the device through the open reservoir.

In use, biological fluid is introduced into the open reservoir 70 and contacts the reagent pad 50. The biological fluid reconstitutes the dried reagent on the reagent pad 50 and begins the clotting or agglutinating process. The biological fluid and reconstituted reagent are drawn into channel 60 connected to the open reservoir 70 by capillary and/or wicking action. The flow of the fluid inside the channel stops when clotting occurs. The channel 60 contains a hydrophilic surface and a precision woven fabric. The surface energies of the hydrophilic surface and the precision woven fabric are carefully adjusted to control both the flow rate and the visual appearance of the end point of the clotting process. The channel 60 can be made of a wide variety of materials in a wide variety of geometric configurations. For example, the channel can be round, rectangular, or oval in shape, and can be made of polymers such as polyethylene, polyester, or polystyrene. Any type of material can be used, so long as it is hydrophilic either inherently or after being treated to render it hydrophilic. Other suitable plastics with high surface free energies and low water sorption that can be used to form the capillary channel include glycol modified polyethylene terephtalate (PETG), polycarbonate, polyvinyl chloride, and styrene-acrylonitrile. However, since these materials are hydrophobic and exhibit poor blood flow, they are preferably rendered hydrophilic by treatment with argon plasma, using a plasma etcher or corona discharge. Suitable conditions are 10–25 watts at 13.56 MHz and one torr chamber pressure for 5–10 minutes. Alternatively, a protein such as albumin can be used to coat the surface by passing a solution through the device having from about 1–5% serum albumin, allowing the solution to stand for 30 minutes, wiping, and drying. Plasma etching and corona discharge provide markedly superior hydrophilicity, thus enhancing the capillary action of the device.

The void volume of the channel is the most important parameter with respect to precision and accuracy of the device. The dimensions of the channel are preferably maintained to a fine tolerance. A typical dimension for the channel is about 0.8–1.2 mm in width, about 0.08–0.12 mm in and about 5 cm to about 15 cm in total length. Preferably, the channel is 1 mm in width, 0.1 mm in height, and 10 cm in length. The hydrophilic channel provides a self-metering feature for the device.

The hydrophilic character of the materials used for making devices according to the present invention must be carefully controlled. The surface energies of these surfaces should be in the range of about 35 to about 70 dynes per cm. This can be tested using calibrated dyne testing solution (Diversified Enterprise, Clairmont, N.H.). The hydrophilic character of the surfaces can be controlled by surface treatments known in the art, such as corona discharge or plasma treatment. Alternatively, or in conjunction with such treatment, a hydrophilic polymer such as polystyrene doped with AMPACET™ anti-fog additive (Ampacet, Tarrytown, N.Y.) can be used for making the channel, or a hydrophilic coating such as polyvinyl alcohol or protein or a blended coating can be applied and dried onto a non-hydrophilic surface to achieve the desired hydrophilicity to enhance capillary flow through the capillary channel.

The precision woven fabric 30 inside the channel 60 is an important element of the device. The fabric inside the channel helps to control the flow rate of the sample fluid and provides the clotting or agglutinating mixture a place to anchor itself, thus providing a very sharp visual end point. For purposes of the present invention, "precision woven fabric" means a fabric which is woven with precise dimensions, i.e., the dimensions required for trapping a clot in the capillary channel, as set forth below. Without a precision woven fabric in the channel 60, the clotted or agglutinated mixture will continue to move, albeit slowly, after the clotting or agglutinating process, making it impossible to read the end point accurately. The precision woven fabric can be made of suitable materials such as polyester, polyethylene, nylon, or other polymers or copolymers. The mesh size of the fabric should be from about 105 to about 526 microns. When the mesh size is greater than about 526 microns, only one or two threads run the length of the open channel, and the benefit of the woven fabric for flow control and anchor support is lost. When the mesh size is below about 105 microns, the weave is too dense to act as a flow control and anchor support, and is more in the nature of a smooth rather than a woven surface.

Figure 2A:
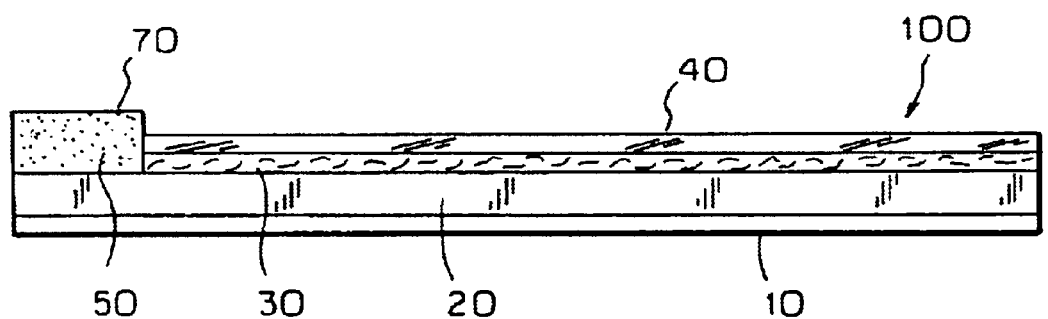
FIG. 2a shows the optional reagent pad located on the top of the channel.
Figure 2B:
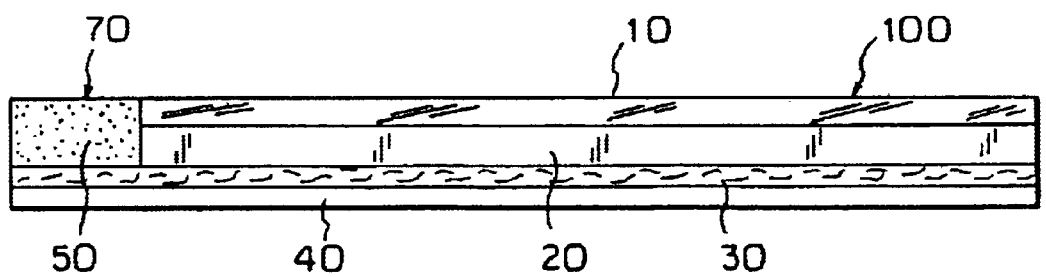
FIG. 2b shows the optional reagent pad located on the bottom of the channel.

FIGS. 2a and 2b show side views of the device 100. FIG. 2a shows the optional reagent pad 50 located on the top of the capillary flow channel (not shown). FIG. 2b shows the optional reagent pad 50 located on the bottom of the capillary flow channel (not shown).

The method and apparatus of the present invention are used to measure the prothrombin time of whole blood, as well as other specific assays using the clotting principle can also be conducted with this method and device. Examples of these include other coagulation tests such as activated prothrombin time, mastitis test using the California Mastitis Test reagent, entodoxin test using the LAL reagent, latex agglutination immunoassays, and lactin based agglutination tests. If the test is one in which a clot or agglutination forms within a certain period of time, the test can be conducted in the device of the present invention. The length of the bar formed prior to the clotting or agglutinating event may be adjusted for different assays by altering the surface energy or dimensions of the capillary channel, depending on the particular assay to be conducted.

More than one scale on the device may be desirable. Although citrated plasma and citrated whole blood scale factors or straight line equations have been observed to be essentially identical for a given batch of reagent, the scale factor for blood including an anticoagulant is typically different. It is therefore important to identify the sample and then select the appropriate scale factor.

The scale factor mat be obtained by comparing clotting or agglutinating results using the sample type plotted against the results of the same samples run as samples on a conventional analyzer. One then obtains the equation or table which compares the two sets of values, which is then used as a scale factor.

It will be clear to those skilled in the art that the method and device of the present invention may equally be used to measure the propensity of a liquid to change from a coagulated state to a liquid state. After clotting of the test sample has occurred, the clot may be subjected to a lytic agent which returns the sample to the liquid state. In this case, the "clotting event" that is measured is the dissolution of the clot by the reagent in the device.

The following examples are provided as specific embodiments of the present invention, and are not intended to limit either the device or method of the present invention.

EXAMPLE 1

An individual test device for prothrombin time is constructed by using a hydrophilic polymer coated plastic (Adhesive Research, PA), of the bottom of the device 10. Polyester spaces 20 are added on two sides of the bottom 10 to form a flow channel 60. A clear polyester backed polyester precision woven fabric (mesh size 105, Sefar, N.Y.) with the fabric on the top side is placed onto the base. The flow channel has a width of 1 mm and a length of 13 cm. The reagent pad 50 is made of high density polyethylene (Porex, Fla.). The air-dried activator was recombinant thromboplastin from International Technidyne Corp (ITC, Edison, N.J.). Thirty five microliters of fingerstick whole blood was deposited into the sample well 70, and the bar length of the clotted red colored whole blood sample was recorded at the end point. A normal sample with 1.2 INR units gave a sharp and flat end point with a bar length of 4.8 cm. An abnormal sample with 4.8 INR units gave a sharp and flat end point with a bar length of 9.9 cm.

For a prothrombin time test, the INR units correlate directly with a shorter bar length. That is, the lower the INR units, the faster is the PT time, and thus the shorter is the bar length. The scale on the capillary channel is calibrated by using control samples. Changing the width of the height or the width of the channel changes the volume, and it is important that the channel width not be too wide so that the blood is able to travel a measurable distance prior to the clotting event.

EXAMPLE 2

Precision studies were carried out with normal and abnormal control samples with devices constructed as in Example 1. With n=10 runs per sample type, the precision obtained was 9.0% for the normal samples and 10.4% for the abnormal samples based on bar length measurements. Comparison studies with a POC PT instrument (ProTime, ITC, Edison, N.J.) yielded a correlation coefficient of 0.87 using whole blood samples with a range of 1.0 to 4.0 INR units.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

All references cited herein are hereby incorporated in their entirety.

What is claimed is:

1. An analytical device for detecting a clotting or agglutinating event in a clottable or agglutinatable biological fluid comprising:
   a. a sample accepting area comprising a reagent to react with the clottable or agglutinatable biological fluid to produce a clot or agglutinate;
   b. a capillary flow channel means through which the fluid may flow and in which the clotting or agglutinating event can occur;
   c. a control means within the capillary flow channel for controlling the flow rate of the clottable or agglutinatable biological fluid and which stops the flow of the clottable or agglutinable biological fluid once the clot or agglutinate has formed.

2. The analytical device according to claim 1 wherein the precision woven fabric has a mesh size of from about 105 microns to about 526 microns.

3. The analytical device according to claim 1 wherein the capillary flow channel is about 0.8 mm to about 1.2 mm in width, from about 0.08 to about 0.12 mm in height, and from about 5 to about 15 cm in length.

4. The analytical device according to claim 3 wherein the capillary flow channel is about 1 mm in width, about 0.1 mm in height, and about 10 cm in length.

5. The analytical device according to claim 1 wherein the surface energy of at least one surface of the capillary flow channel is from about 35 to about 70 dynes per cm.

6. The analytical device according to claim 1 wherein the reagent is carried in a reagent pad located in the sample accepting area.

7. A method for measuring the clotting or agglutination time of a sample comprising:
   a. introducing a sample into an analytical device according to claim 1;
   b. allowing the sample to contact the reagent and flow through the capillary flow channel forming a colored bar until clotting or agglutination occurs and;
   c. measuring the length of the colored bar.

8. The method according to claim 7 wherein prothrombin time is measured.

9. The method according to claim 7 wherein agglutination of latex beads in a sample is measured.

10. In an analytical device for detecting a clotting or agglutination event in a fluid, the improvement comprising detecting the event in a capillary flow channel wherein the capillary flow channel contains a fabric means therein for controlling the flow rate of the fluid by stopping the flow and trapping a clot or agglutinate therein once clotting or agglutination has occurred.

11. The device according to claim 10 wherein the fabric means is a precision woven fabric.

12. The device according to claim 11 wherein the precision woven fabric has a mesh of from about 105 microns to about 526 microns.

* * * * *

UNITED STATES PATENT AND TRADEMARK OFFICE
CERTIFICATE OF CORRECTION

| | | |
|---|---|---|
| PATENT NO. | : 6,759,009 B2 | Page 1 of 1 |
| APPLICATION NO. | : 10/138718 | |
| DATED | : July 6, 2004 | |
| INVENTOR(S) | : Wai Tak Law | |

It is certified that error appears in the above-identified patent and that said Letters Patent is hereby corrected as shown below:

In the claims:

In Column 7, Line 30, in Claim 1 b., delete "means" and insert -- connected to the sample accepting area --

In Column 7, Line 32, in Claim 1 b., after the word "occur;", insert -- and --

In Column 7, Line 35, in Claim 1 c., delete "which stops" and insert -- wherein the control means is a fabric woven so as to stop --

In Column 7, Line 37, in Claim 1 c., after the word "formed", insert -- by trapping the clot or agglutinate therein --

In Column 7, Line 39, in Claim 2, delete "precision woven"

In Column 8, Line 21, in Claim 7 b., change the location of ";" from "and ;" to ";and"

Signed and Sealed this
Twenty-sixth Day of August, 2014

Michelle K. Lee
*Deputy Director of the United States Patent and Trademark Office*